(12) United States Patent
Wojcik et al.

(10) Patent No.: US 8,192,100 B2
(45) Date of Patent: Jun. 5, 2012

(54) FLUID APPLICATOR DEVICE AND METHOD OF USING SAME

(75) Inventors: Michael Wojcik, Plainfield, IL (US); Kelly Sanborn, Naperville, IL (US)

(73) Assignee: Blistex Inc., Oak Brook, IL (US)

( * ) Notice: Subject to any disclaimer, the term of this patent is extended or adjusted under 35 U.S.C. 154(b) by 948 days.

(21) Appl. No.: 11/593,347

(22) Filed: Nov. 6, 2006

(65) Prior Publication Data

US 2008/0107475 A1 May 8, 2008

(51) Int. Cl.
*B43K 7/10* (2006.01)
(52) U.S. Cl. .......................... 401/216; 401/175; 401/209
(58) Field of Classification Search .................. 401/208, 401/216, 217, 219, 220, 175, 209
See application file for complete search history.

(56) References Cited

U.S. PATENT DOCUMENTS

| 3,212,120 | A  | * | 10/1965 | Gentile ......................... 401/175 |
| 3,781,123 | A  | * | 12/1973 | Linz et al. ..................... 401/216 |
| 5,553,957 | A  | * | 9/1996  | Dornbusch et al. ........... 401/209 |
| 6,481,910 | B1 | * | 11/2002 | Yang ............................. 401/175 |
| 7,153,053 | B1 | * | 12/2006 | Wiley ........................... 401/219 |

* cited by examiner

*Primary Examiner* — David Walczak
(74) *Attorney, Agent, or Firm* — Ladas & Parry LLP

(57) ABSTRACT

A fluid applicator device having the interconnected components of a container, a base, a shaft, a piston, a collar, a plurality of fluid conduction pathways and an applicator head is presented. The applicator head is rotatably mounted within the collar and slidably held in place by the inner surface of the collar. The inner surface of the collar also has a plurality of fluid conduction pathways cut into it so that a viscous fluid confined within the container may be flow into the fluid conduction pathways and onto the applicator head so that it may be soothingly applied onto a portion of a user's epidermis such as onto the lips of a user. The method of using the applicator device includes the acts of manipulating, obtaining, pressing, removing, returning, rolling, and withdrawing.

18 Claims, 3 Drawing Sheets

FLUID APPLICATOR DEVICE AND METHOD OF USING SAME

FIELD OF THE INVENTION

The present invention relates to a fluid applicator. More particularly, it concerns fluid applicator devices and associated methods of using the devices that are especially adapted to apply fluids onto the epidermis of humans. The present invention has particular utility in applying viscous fluids such as cosmetic creams, lipstick substrates, lotions, lip care moisturizing products, and pharmaceutical products onto lips.

DESCRIPTION OF THE PRIOR ART

A large variety of liquid applicators have been disclosed in the prior art. Perhaps one of the most widely used applicators is of the so-called ball roll-on type applicator. These are exemplified in U.S. Pat. Nos. 2,749,566; 2,923,957 and 2,998,616 and rely on the fact that the ball rotating in the liquid contained in a bottle picks up the liquid as it dips into the contents of the container and applies it to the body area on which the ball is rolled.

Although these applicators have enjoyed wide use, they are unsuitable for use in applying thicker products. Unfortunately, only thin or very low viscosity liquids can be easily applied with these types of applicators which sometimes requires the user to invert the applicator in order to dispense these thin liquid products.

It has also been suggested in the prior art to construct liquid applicators which comprise a container for holding the fluid to be dispensed and an applicator means positioned on the open end of the container; the applicator means comprising a distortable porous or microporous member. These porous members, in general, are in communication with the fluid contents of the container and they permit the fluid material to flow through its pores. However, these devices ordinarily require that the applicator means be mechanically or otherwise squeezed to deliver the product. Typical devices of this character are described in U.S. Pat. Nos. 3,179,972 and 3,482,920. Devices of these types often suffer the disadvantage in that it is substantially difficult to deliver onto the epidermis sufficient quantities of relatively high viscosity fluids from the contents of the container. This is so because the quantity of fluid material delivered to a substantial extent is dependent upon the pressure that is applied when dispensing these materials. This pressure cannot readily be regulated from one application to another.

A wide variety of applicator devices is currently available on the commercial market and an even larger number of these types of devices are known in the art of applicator devices, for example the clear roll-on bottle disclosed by Yorks in U.S. Pat. No. 5,051,017; the sealable toiletry article disclosed by Roberts in U.S. Pat. No. 6,637,966; the roll-on dispenser with a flexible membrane disclosed by Mackles in U.S. Pat. No. 4,342,522; the sun lotion applicator disclosed by Scuderi in U.S. Pat. No. 4,571,106; the roll-on dispenser bottle assembly disclosed by Lench et al. in U.S. Pat. No. 4,030,844; the elongated roll-on applicator package with resilient liner disclosed by Fattori et al. in U.S. Pat. No. 4,840,511; the fluid ball applicator with vent tube disclosed by Kim in U.S. Pat. No. 4,940,350; the liquid applicator disclosed by Berghahn et al. in U.S. Pat. No. 4,050,826; the deer feeder disclosed by Fore in U.S. Pat. No. 5,143,022; the closure for roll-on applicator disclosed by Weinstein in U.S. Pat. No. 4,588,320; the deodorant antiperspirant cap activated wide-roll-on disclosed by Bengston in U.S. Pat. No. 5,051,016; the ball roll-on dispenser disclosed by Berghahn et al. in U.S. Pat. No. 4,021,125; the roll-on applicator disclosed by Breidenbach et al. in U.S. Pat. No. 6,939,071; the liquid applicator disclosed by Yasunaga et al. in U.S. Pat. No. 5,709,492; and the device having a magnetic applicator and/or wiper member disclosed by Gueret in U.S. Pat. No. 6,866,437.

While all of the above-described devices fulfill their respective, particular objectives and requirements, the aforementioned patents do not describe an applicator device having a container, a base, a shaft, a piston, a collar, a plurality of fluid conduction pathways, and an applicator head rotatably mounted within the collar and so that a viscous fluid held within the container may easily flow into the fluid conduction pathways and onto the applicator head to soothingly present the viscous fluid onto a user's lips.

This combination of elements would specifically match the user's particular individual needs of making it possible to provide a convenient means for applying a relatively viscous fluid onto a portion of an epidermis of a user. The above-described patents make no provision for an applicator device having a container, a base, a shaft, a piston, a collar, a plurality of fluid conduction pathways, and an applicator head rotatably mounted within the collar in which a fluid held within the container may flow into the fluid conduction pathways and onto the applicator head so that the fluid may be rolled onto a user's epidermis, such as a user's lips.

Therefore, a need exists for a new and improved applicator device having the interconnected components of a container, a base, a shaft, a piston, a collar, a plurality of fluid conduction pathways, and an applicator head rotatably mounted within the collar so that a viscous fluid held within the container may flow into the fluid conduction pathways and onto the applicator so that the fluid may be soothingly rolled onto a user's epidermis, such as a user's lips. In this respect, the applicator device according to the present invention substantially departs from the conventional concepts and designs of the prior art, and in doing so provides an apparatus primarily developed for the purpose of providing a convenient and soothing means for applying a relatively viscous fluid onto a portion of an epidermis of a user.

SUMMARY OF THE INVENTION

The present device and method of using, according to the principles of the present invention, overcomes a number of the shortcomings of the prior art by providing a novel applicator device and method for use in applying fluid materials. The applicator device includes a container, a base, a shaft, a piston, a collar, a plurality of fluid conduction pathways so that a viscous fluid held within the contain may flow into the fluid conduction pathways and onto the applicator head so that the fluid may be gently rolled onto a user's epidermis, such as a user's lips. The method includes the acts of manipulating, obtaining, pressing, removing, returning, rolling, and withdrawing.

In view of the foregoing disadvantages inherent in the known type applicator devices and method for use now present in the prior art, the present invention provides an improved applicator device, which will be described subsequently in great detail, is to provide a new and improved applicator device which is not anticipated, rendered obvious, suggested, or even implied by the prior art, either alone or in any combination thereof.

To attain this, the present invention essentially comprises an applicator device having the interconnected elements of a container, a base, a shaft, a piston, a collar, a plurality of fluid conduction pathways, and an applicator head rotatably mounted within the collar in which a fluid held within the container may conveniently flow into the fluid conduction pathways and onto the applicator head so that the fluid may be gently rolled onto a user's epidermis, such as a user's lips.

There has thus been outlined, rather broadly, the more important features of the invention in order that the detailed description thereof that follows may be better understood, and in order that the present contribution of the art may be better appreciated.

The invention may also include a number of optional elements, such as a cap, a fluid, a rim, and a pliable seal.

Numerous objects, features and advantages of the present invention will be readily apparent to those of ordinary skill in the art upon reading of the following detailed description of presently preferred, but nonetheless illustrative, embodiments of the present invention when taken in conjunction with the accompany drawings. In this respect, before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an aspect of the present invention to provide a new and improved applicator device that has many of the advantages of the prior applicator devices and minimizing a number of their disadvantages.

It is another aspect of the present invention to provide a new and improved applicator device that may be easily and efficiently manufactured and marketed.

An even further aspect of the present invention is to provide a new and improved applicator device that has a low cost of manufacture with regard to both materials and labor, and which accordingly is then susceptible of low prices of sale to the consuming public, thereby making applicator devices economically available to the buying public.

Still another aspect of the present invention is to provide an applicator device that bestows a smooth sensation when applying a fluid product onto the user's epidermis from a roller ball applicator, in particular using a smooth metal roller ball applicator to apply a fluid to the user's lips.

Yet another aspect of the present invention is to provide an applicator device that avoids the need to invert the roller ball applicator in order to apply the dispersant fluid.

Still yet another aspect of the present invention is to provide an applicator device that can dispense relatively high viscosity fluids onto a user's epidermis rather than thin, short-lasting liquids.

Even still another aspect of the present invention is to provide an applicator device having the interconnected elements of a container, a base, a shaft, a piston, a collar, a plurality of fluid conduction pathways, and an applicator head rotatably mounted within the collar so that a fluid held within the container may flow into the fluid conduction pathways and onto the applicator head so that the fluid may be rolled onto a users epidermis such as a user's lips.

Lastly, it is an aspect of the present invention to provide a new and improved method of using an applicator device comprising the acts of manipulating, obtaining, pressing, removing, returning, rolling, and withdrawing.

Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be had to the accompanying drawings and description matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various figures.

DETAILED DESCRIPTION OF THE PREFERRED EMBODIMENT

Figures 1, 2:
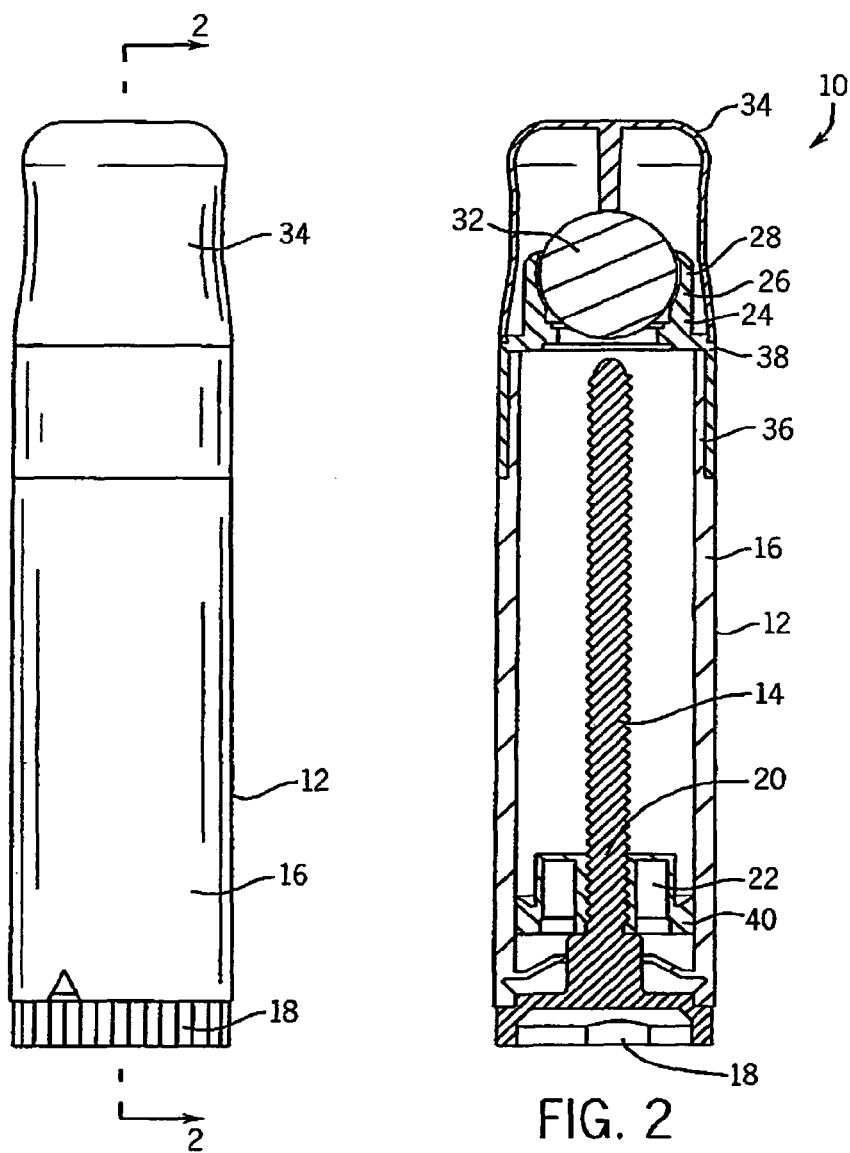
FIG. 1 is a longitudinal side view of an embodiment of the applicator device constructed in accordance with the principles of the present invention.
FIG. 2 is a cross sectional longitudinal side view of an embodiment of the applicator device constructed in accordance with the principles of the present invention.

Referring now to the drawings, and in particular FIGS. 1 to 5 thereof, one preferred embodiment of the present invention is shown and generally designated by the reference numeral 10. One preferred embodiment of the applicator device 10 comprises a container 12, a base 18, a shaft 20, a piston 22, a plurality of fluid conduction pathways 30, and an applicator head 32. The container 12 has an interior and exterior surface (14 and 16, respectively). The base 18 is attached to the container 12. The shaft 20 is attached to the base 18. The piston 22 is attached to the shaft 20 in which the piston 22 is configured to be slidably fitted against the interior surface 14 of the container 12. The collar 24 is attached to the container 12 in which the collar 24 has an inner surface 26 and an outer surface 28. The plurality of fluid conduction pathways 30 are cut into the inner surface 26 of the collar 24. The applicator head 32 is rotatably mounted within the collar 24 in which the applicator head 32 is slidably attached to the inner surface 26 of the collar 24 so that the applicator head 32 is rotatable about the plurality of fluid conduction pathways 30.

The container 12 may be any geometric shape. One preferred embodiment of the exterior surface 16 of the container 12 is that it has a generally cylindrical shape.

The applicator head 32 may have any geometric shape as long as it is partially confined within the inner surface 26 of the collar 24 and rotatably mounted within the collar 24. One embodiment of the applicator head 32 is that it has a generally spherical shape. Another embodiment of the applicator head 32 is that it has a generally elongated cylindrical shape. Still another embodiment of the applicator head 32 is that it has a generally ellipsoidal shape. Another embodiment is that the collar 24 substantially complementarily matches the surface of the applicator head 32 so that the applicator head 32 is in physical contact with collar 24.

The fluid conduction pathways 30 may have any geometric shape as long as a fluid 36 can pass from the interior of the container onto the surface of the applicator head and be delivered onto the epidermis of the user. One embodiment of each fluid conduction pathway 30 is that each has a width of at least 0.2 mm. Another embodiment of each fluid conduction pathway 30 is that each has a width of at least 0.5 mm.

An optional cap 34 may be attached to the collar 24.

An optional fluid 36 may be enclosed within the container 12, the piston 22 and the applicator head 32. A number of preferred embodiments of the fluid 36 is it may be selected from the group consisting of a cosmetic cream, a lipstick substrate, a lotion, a lip care moisturizing product, and a pharmaceutical. One embodiment of the fluid 36 is that is has a viscosity of at least 20 centistokes at about 25 degrees centigrade. Another embodiment of the fluid 36 is that is has a viscosity of at least 50 centistokes at about 25 degrees centigrade. Still another embodiment of the fluid 36 is that is has a viscosity of at least 100 centistokes at about 25 degrees centigrade. Yet another embodiment of the fluid 36 is that it has a viscosity of at least 200 centistokes at about 25 degrees centigrade. Even yet another embodiment of the fluid 36 is that it is in the form of a water-in-oil emulsion having an oily phase and an aqueous phase, the fluid 36 comprising, by weight: about 0.5 to 35% of at least one fatty acid ester; about 0.5 to 29% of at least one hydrocarbon wax; the total of the at least one fatty acid ester and the at least one hydrocarbon wax being at least about 1.0%; about 0.2 to 30% of liposomes; and about 1 to 7% of an emulsifier system consisting essentially of behenoyl stearate in combination with sodium borate, the oily phase comprising the at least one fatty acid ester, the at least one wax, and the emulsifier system.

An optional rim 38 may be attached to the collar 24 in which the rim 38 and the cap 34 may be configured to be snap fitted together.

An optional pliable seal 40 may be attached to the piston 22 so that the pliable seal 40 press fits against the interior surface 14 of the container 12.

One embodiment of a method of using an applicator device 10 comprises the acts of manipulating, obtaining, pressing, removing, returning, rolling, and withdrawing. The obtaining act comprises obtaining the applicator device 10 comprising: a container 12 having an interior and exterior surface (14 and 16, respectively); a base 18 attached to the container 12; a shaft 20 attached to the base 18; a piston 22 attached to the shaft 20, wherein the piston 22 is configured to be slidably fitted against the interior surface 14 of the container 12; a collar 24 attached to the container 12, the collar 24 having an inner surface 26 and an outer surface 28; a plurality of fluid conduction pathways 30 cut into the inner surface 26; an applicator head 32 rotatably mounted within the collar 24, the applicator head 32 slidably attached to the inner surface 26 of the collar 24 so that the applicator head 32 is rotatable about the plurality of fluid conduction pathways 30; a cap 34 configured to be attached to the collar 24; and a fluid 36 enclosed within the container 12, the piston 22 and the applicator head 32. The removing act comprises removing the cap 34 from the collar 24. The manipulating act comprises manipulating the base 18 so that a portion of the fluid 36 oozes through the plurality of fluid conduction pathways 30 onto the applicator head 32. The pressing act comprises pressing the applicator head 32 onto a lip of a user. The rolling act comprises rolling the applicator head 32 over a portion of the users lips to dispense a portion of the oozed fluid 36 onto the lip of the user. The withdrawing act comprises withdrawing the applicator head 32 away from the lip of the user. The returning act comprises returning cap 34 onto the collar 24.

Referring now to FIG. 1 that depicts a longitudinal side view of an embodiment of the applicator device showing the exterior surface 16 of the container 12; the base 18 attached to the container 12; and the optional cap 34 attached to the container 12.

Referring now to FIG. 2 that depicts a longitudinal cross section view of an embodiment of the applicator device 10 showing a container 12 having an interior and exterior surface (14 and 16 respectively); a base 18 attached to the container 12; a shaft 20 attached to the base 18; a piston 22 attached to the shaft 20, wherein the piston 22 is configured to be slidably fitted against the interior surface 14 of the container 12; a collar 24 attached to the container 12, the collar 24 having an inner surface 26 and an outer surface 28; a plurality of fluid conduction pathways 30 cut to the inner surface 26 of the collar 24; an applicator head 32 rotatably mounted within the collar 24, the applicator head 32 slidably attached to the inner surface of the 26 of the collar 24 so that the applicator head 32 is rotatable about the plurality of fluid conduction pathways 30; a cap 34 configured to be attached to the collar 24; a fluid 36 enclosed within the container 12, the piston 22 and the applicator head 32; a pliable seal 40 attached to the piston 22, the pliable seal 40 press fit against the interior surface 14 of the container 12; and a rim 38 attached to the collar 24.

Figure 3:
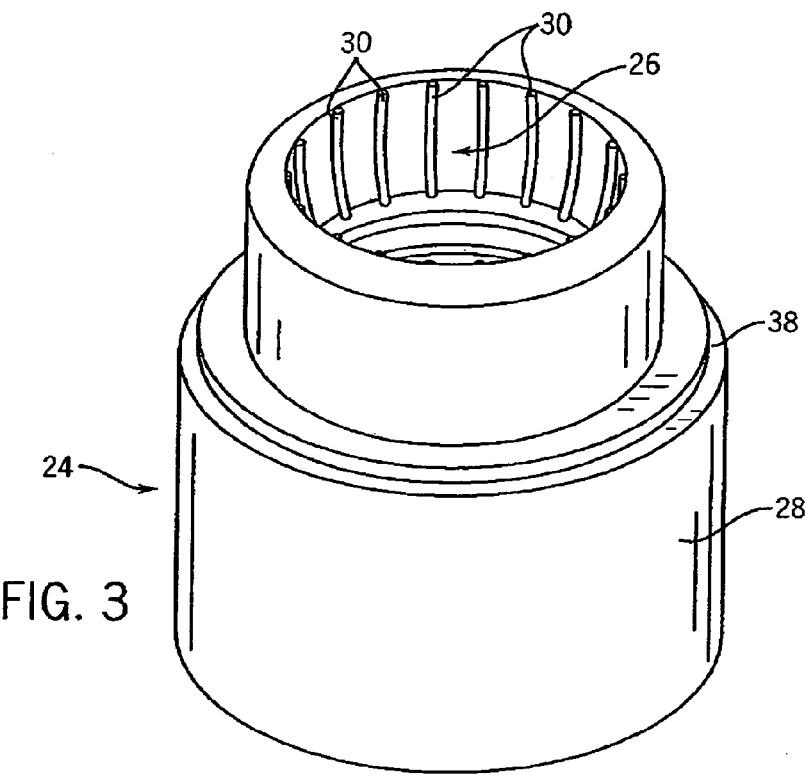
FIG. 3 is a perspective view of a collar of the applicator device of the present invention.

FIG. 3 is a perspective view of a collar of the applicator device of the present invention;

Referring now to FIG. 3 that depicts a perspective view of a collar 24 of an embodiment of the applicator device 10 of the present invention. Note that the applicator head 32 is not depicted. The fluid conduction pathways 30 are shown cut into to the inner surface 26 of the collar 24. Also shown is the optional rim 38 attached to the collar 24.

Figure 4:
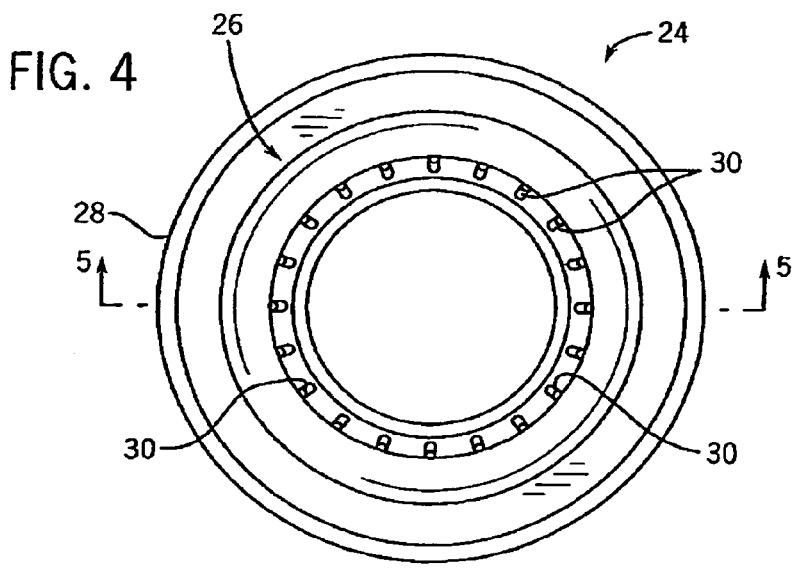
FIG. 4 is a front view of the collar of the applicator device of the present invention.

Referring now to FIG. 4 that depicts a front view of a collar 24 of an embodiment of the applicator device 10 of the present invention. Note that the applicator head 32 is not depicted. The fluid conduction pathways 30 are shown cut into the inner surface 26 of the collar 24.

Figure 5:
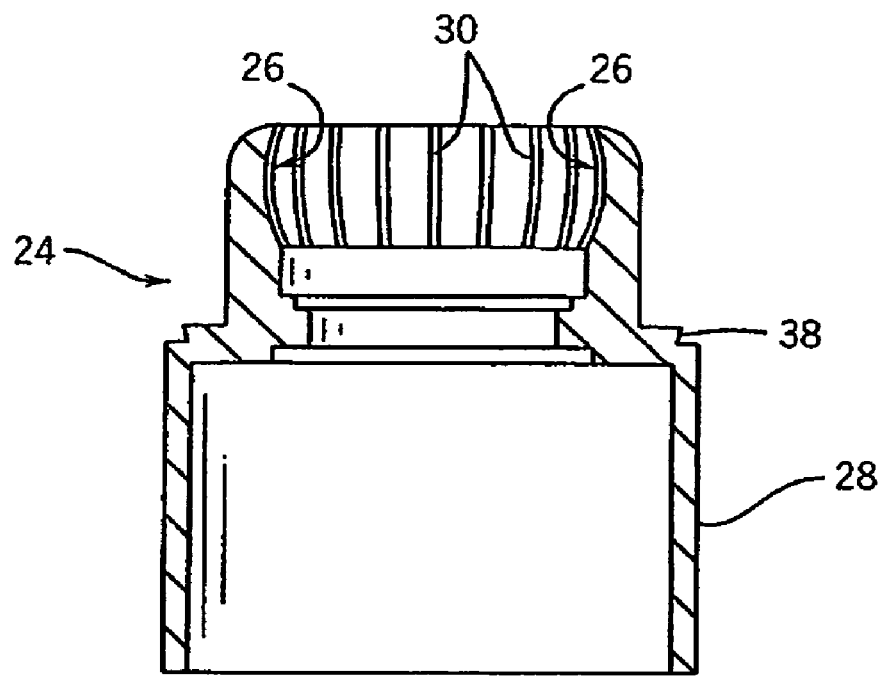
FIG. 5 is a cross sectional longitudinal side view of the collar of the applicator device of the present invention.

Referring now to FIG. 5 that depicts a cross sectional longitudinal side view of a collar of an embodiment of the applicator device 10 of the present invention. Note that the applicator head 32 is not depicted. Shown are the interior surface 26 and the exterior surface 28 of the collar 24.

As to the manner of usage and operation of the present invention, the same should be apparent from the above description. Accordingly, no further discussion relating to the manner of usage and operation will be provided.

While a preferred embodiment of the applicator device 10 and associated methods for using the device 10 have been described in detail, it should be apparent that modifications and variations thereto are possible, all of which fall within the true spirit and scope of the invention. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Throughout this specification, unless the context requires otherwise, the word "comprise" or variations such as "comprises" or "comprising" or the term "includes" or variations, thereof, or the term "having" or variations, thereof will be understood to imply the inclusion of a stated element or integer or group of elements or integers but not the exclusion of any other element or integer or group of elements or integers. In this regard, in construing the claim scope, an embodiment where one or more features is added to any of the claims is to be regarded as within the scope of the invention given that the essential features of the invention as claimed are included in such an embodiment.

Those skilled in the art will appreciate that the invention described herein is susceptible to variations and modifications other than those specifically described. It is to be understood that the invention includes all such variations and modification that fall within its spirit and scope. The invention also includes all of the steps, features, compositions and compounds referred to or indicated in this specification, individually or collectively, and any and all combinations of any two or more of said steps or features.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. An applicator device comprising:
   a container having an interior and exterior surface;
   a base attached to the container;
   a shaft attached to the base;
   a piston attached to the shaft, wherein the piston is configured to be slidably fitted against the interior surface of the container;
   a collar attached to the container, the collar having an inner surface and an outer surface;
   a plurality of fluid conduction pathways cut into the inner surface of the collar and in which said pathways extend vertically to an upper edge of the collar; and
   an applicator head rotatably mounted within the collar wherein a portion of said applicator head extends beyond said upper edge to thereby enable said applicator head to apply product to a surface, the applicator head slidably attached to the inner surface of the collar so that the entire applicator head is rotatable about and in contact with the plurality of fluid conduction pathways circumferentially deployed about the inner surface.

2. The device of claim 1 further comprising a cap attached to the collar.

3. The device of claim 2 further comprising a rim attached to the collar, wherein the rim and the cap are configured to be snap-fitted together.

4. The device of claim 1 further comprising a fluid enclosed within the container, the piston and the applicator head.

5. The device of claim 4 wherein the fluid is selected from the group consisting of a cosmetic cream, a lipstick substrate, a lotion, a lip care moisturizing product, and a pharmaceutical.

6. The device of claim 4 wherein the fluid having a viscosity of at least 20 centistokes at about 25 degrees centigrade.

7. The device of claim 4 wherein the fluid having a viscosity of at least 50 centistokes at about 25 degrees centigrade.

8. The device of claim 4 wherein the fluid having a viscosity of at least 100 centistokes at about 25 degrees centigrade.

9. The device of claim 4 wherein the fluid having a viscosity of at least 200 centistokes at about 25 degrees centigrade.

10. The device of claim 4 wherein the fluid enclosed within the container is in the form of a water-in-oil emulsion having an oily phase and an aqueous phase, the fluid comprising, by weight: about 0.5 to 35% of at least one fatty acid ester;
    about 0.5 to 29% of at least one hydrocarbon wax; the total of said at least one fatty acid ester and said at least one hydrocarbon wax being at least about 1.0%; about 0.2 to 30% of liposomes; and about 1 to 7% of an emulsifier system consisting essentially of behenoyl stearate in combination with sodium borate, said oily phase comprising said at least one fatty acid ester, said at least one wax, and said emulsifier system.

11. The device of claim 1 further comprising a pliable seal attached to the piston, the pliable seal press fit against the interior surface of the container.

12. The device of claim 1 wherein the exterior surface of the container having a generally cylindrical shape.

13. The device of claim 1 wherein the applicator head having a generally spherical shape.

14. The device of claim 1 wherein the collar substantially complementarily matches the surface of the applicator head so that the applicator head is in physical contact with collar.

15. The device of claim 1 wherein each fluid conduction pathway having a width of at least 0.2 mm.

16. The device of claim 1 wherein each fluid conduction pathway having a width of at least 0.5 mm.

17. An applicator device comprising:
    a container having an interior and exterior surface;
    a base attached to the container;
    a shaft attached to the base;
    a piston attached to the shaft, wherein the piston is configured to be slidably fitted against the interior surface of the container;
    a collar attached to the container, the collar having an inner surface and an outer surface;
    a plurality of fluid conduction pathways cut into the inner surface of the collar and in which said pathways extend vertically to an upper edge of the collar;
    an applicator head rotatably mounted within the collar wherein a portion of said applicator head extends beyond said upper edge to thereby enable said applicator head to apply product to a surface, the applicator head slidably attached to the inner surface of the collar so that the entire applicator head is rotatable about and in contact with the plurality of fluid conduction pathways circumferentially deployed about the inner surface;
    a cap configured to be attached to the collar;
    a fluid enclosed within the container, the piston and the applicator head; and
    a pliable seal attached to the piston, the pliable seal press fit against the interior surface of the container.

18. A method of using an applicator device, said method comprising the acts of: obtaining the applicator device comprising:
- a container having an interior and exterior surface;
- a base attached to the container,
- a shaft attached to the base;
- a piston attached to the shaft, wherein the piston is configured to be slidably fitted against the interior surface of the container,
- a collar attached to the container, the collar having an inner surface and an outer surface;
- a plurality of fluid conduction pathways cut into the inner surface of the collar and in which said pathways extend vertically to an upper edge of the collar;
- an applicator head rotatably mounted within the collar wherein a portion of said applicator head extends beyond said upper edge to thereby enable said applicator head to apply product to a surface, the applicator head slidably attached to the inner surface of the collar so that the entire applicator head is rotatable about and in contact with the plurality of fluid conduction pathways circumferentially deployed about the inner surface;
- a cap configured to be attached to the collar; and
- a fluid enclosed within the container, the piston and the applicator head; removing the cap from the collar; manipulating the base so that a portion of the fluid oozes through the plurality of fluid conduction pathways onto the applicator head; pressing the applicator head onto a lip of a user; rolling the applicator head over a portion of the users lips to dispense a portion of the oozed fluid onto the lip of the user; withdrawing the applicator head away from the lip of the use; and returning cap onto the collar.

* * * * *